United States Patent
Rozlosnik et al.

(10) Patent No.: US 9,869,652 B2
(45) Date of Patent: Jan. 16, 2018

(54) BIOSENSOR FOR POINT-OF-CARE DIAGNOSTIC AND ON-SITE MEASUREMENTS

(75) Inventors: Noemi Rozlosnik, Bagsvaerd (DK); Johannes Dapra, Copenhagen V (DK)

(73) Assignee: DANMARKS TEKNISKE UNIVERSITET, KGS. Lyngby (DK)

( * ) Notice: Subject to any disclaimer, the term of this patent is extended or adjusted under 35 U.S.C. 154(b) by 958 days.

(21) Appl. No.: 14/343,691

(22) PCT Filed: Sep. 7, 2012

(86) PCT No.: PCT/EP2012/067508
§ 371 (c)(1),
(2), (4) Date: Jul. 1, 2014

(87) PCT Pub. No.: WO2013/034688
PCT Pub. Date: Mar. 14, 2013

(65) Prior Publication Data
US 2014/0311904 A1    Oct. 23, 2014

Related U.S. Application Data

(60) Provisional application No. 61/532,721, filed on Sep. 9, 2011.

(30) Foreign Application Priority Data

Sep. 9, 2011   (EP) .................................. 11180774

(51) Int. Cl.
*C12Q 1/00*      (2006.01)
*G01N 27/327*    (2006.01)
(52) U.S. Cl.
CPC ....... *G01N 27/327* (2013.01); *G01N 27/3275* (2013.01)

(58) Field of Classification Search
CPC ............. G01N 27/327; G01N 27/3271; G01N 27/3275; G01N 27/3278; G01N 33/5438; G01N 33/553; B82Y 15/00; C12C 1/6825
(Continued)

(56) References Cited

U.S. PATENT DOCUMENTS

2012/0122715 A1*  5/2012  Gao .................... G01N 27/3278
                                                              506/9

FOREIGN PATENT DOCUMENTS

WO    WO 2010/104479    *  9/2010    ........... G01N 27/021

OTHER PUBLICATIONS

Song et al. Aptamer-based biosensors, available online Dec. 23, 2007.
(Continued)

*Primary Examiner* — Jill Warden
*Assistant Examiner* — Dwayne K Handy
(74) *Attorney, Agent, or Firm* — Brinks Gilson & Lione

(57) ABSTRACT

Disclosed herein is a biosensor for detection of a target substance in a sample with impedance spectroscopy, the biosensor comprising 1) a first non-conducting substrate comprising a primary substrate surface; 2) a conducting polymer electrode layer comprising one or more conducting polymers layers, the conducting polymer electrode layer comprising a primary electrode surface and a secondary electrode surface, wherein the secondary electrode surface covers part of the primary substrate surface; 3) a probe layer bonded to part of the primary electrode surface; and 4) a second non-conducting substrate comprising a secondary substrate surface, wherein the secondary substrate surface of the second substrate and the primary substrate surface of the first substrate are interconnected such that the electrode layer and the probe layer are confined within an area defined by the first substrate and the second substrate; wherein the
(Continued)

electrode layer comprises at least a first electrode pair, the first electrode pair comprising a primary electrode and a secondary electrode, where the probe layer is bonded to the primary electrode and the secondary electrode of the at least first electrode pair, the probe layer being adapted for selectively binding of the target substance.

19 Claims, 8 Drawing Sheets

(58) Field of Classification Search
USPC .................. 204/400, 403.01, 403.02, 403.03
See application file for complete search history.

(56) References Cited

OTHER PUBLICATIONS

Noemi Rozlosnik New directions in medical biosensors employing poly (3,4-ethylenedioxy thiophene) derivative-based electrode, published Jul. 15, 2009.
Han et al. Design Strategies for Aptamer-based Biosensors, published May 4, 2010.
Katrine Kiilerich-Pedersen Polymer based biosensors for pathogen diagnosyics, published Jul. 18, 2011.
Katrine Kiilerich-Pedersen Polymer based biosensor for rapid electrochemical detection of virus infection of human cells, available online Jul. 28, 2011.
Extended European Search Report for Application EP 11 18 0774, dated Jan. 30, 2012.
International Search Report and Written Opinion for PCT:EP2012:067508, dated Nov. 22, 2012.

\* cited by examiner

BIOSENSOR FOR POINT-OF-CARE DIAGNOSTIC AND ON-SITE MEASUREMENTS

RELATED APPLICATIONS

This application claims the benefit under 35 U.S.C. §371 of International Application No. PCT/EP2012/067508, having an International Filing Date of Sep. 7, 2012, which claims priority to European Application No. EP 11180774.9, filed Sep. 9, 2011, and U.S. Provisional Application No. 61/532,721, filed Sep. 9, 2011, the contents of all of which are incorporated herein by reference in their entirety.

The invention relates to an improved biosensor for fast, easy and reliable point-of-care diagnostics and on-site measurements using impedance spectroscopy.

In a global community, the outbreak of infectious diseases contributes to the fear of severe pandemics, and is a source of worry for the population. In recent years, emerging viruses such as e.g. Dengue virus, West Nile virus, and influenza A virus, have been a focus of massive attention.

Conventional diagnostic methods for detection of acute viral disease count e.g. polymerase chain reactions (PCR) and enzyme linked immunosorbent assays (ELISA). These diagnostic methods give reliable results, but require rather complicated procedures. PCR and ELISA diagnostic methods are time consuming, expensive, labour intensive, and require trained personnel and specialised laboratories.

The demands in modern medical diagnosis thus put forward an enormous need for faster and cheaper detection methods for detecting viral infections, which give a prompt result. If it had been possible to efficiently diagnose humans for Swine-Origin influenza A (H1N1)-virus, back in 2009, treatment could have been applied quickly and the flu might not have been so widespread.

Impedimetric biosensors are a class of biosensors used for detection of e.g. viruses using electrochemical impedance spectroscopy (EIS). When a target substance, such as e.g. a target molecule, binds to an impedance biosensor, it will induce a change in the electrode surface/liquid solution interface. The difference in the impedance measured before and after the target substance binds to the biosensor provides a direct indication of the amount of target substance in the sample. Thus, the presence of a target substance in a sample can be detected very efficiently with a biosensor using electrochemical impedance spectroscopy (EIS).

EIS measures the electrical impedance by imposing a small sinusoidal voltage at a certain frequency to an electrochemical cell and measuring the resulting current through the cell. The time dependent current-voltage ratio and the phase shift give the impedance. Since the impedance changes when the target analyte is captured on the surface of the electrodes, EIS represents a powerful method for probing the interfacial reactions of modified electrodes, providing a rapid approach for monitoring the dynamics of biomolecular interactions.

The impedance of a system is frequency dependent, and can be expressed as a complex number:

$$Z(f) = Z_0(\cos(\varphi) + i \sin(\varphi)) \quad [1]$$

where f is the frequency, $Z_0$ is the magnitude of the impedance, and $\varphi$ is the phase shift. Thus, the impedance $Z(f)$ consists of a real and an imaginary part. The graph, on which the imaginary part of the impedance is plotted against the real part (so-called "Nyquist Plot"), can be used to determine the most efficient frequency for the detection of the target binding.

Impedance biosensors are very promising for a variety of applications such as point-of-care diagnostics, on-site measurements, consumer test kits, bioprocess monitoring, water quality testing, and biowarfare agent detection, due to among others the advantage of label-free operation.

Especially point-of-care diagnostic applications (diagnostic testing at or near the site of patient care) are promising in connection with impedance biosensors, as it brings the test conveniently and immediately to the patient, facilitating rapid treatment.

Existing technologies for point-of-care diagnostics, often based on laminar flow assays (LFA), are usually not very specific and have high detection limits.

Today, screening of blood samples for disease markers is expensive both in hours and reagents. Further, screenings are labour intensive and need to be conducted in specialised laboratories by trained personnel. Accordingly it is an object of the invention to provide an improved, user friendly and cheap biosensor for point-of-care testing and onsite diagnostics.

Disclosed herein is a biosensor for detection of a target substance in a sample with impedance spectroscopy. The biosensor comprises 1) a non-conducting substrate comprising a primary substrate surface; 2) a conducting polymer electrode layer comprising one or more conducting polymers layers, the conducting polymer electrode layer comprising a primary electrode surface and a secondary electrode surface, wherein the secondary electrode surface covers part of the primary substrate surface; 3) a probe layer bonded to part of the primary electrode surface; and 4) a second non-conducting substrate comprising a secondary substrate surface, wherein the secondary substrate surface of the second substrate and the primary substrate surface of the first substrate are interconnected such that the electrode layer and the probe layer are confined within an area defined by the first substrate and the second substrate; wherein the electrode layer comprises at least a first electrode pair, the first electrode pair comprising a primary electrode and a secondary electrode, where the probe layer is bonded to the primary electrode and/or the secondary electrode of the at least first electrode pair, the probe layer being adapted for selectively binding of the target substance.

Examples of materials for the first and the second substrate comprise glass, non-conducting polymers and similar. By non-conducting polymer is meant a polymer with a conductivity of less than $10^{-8}$ S/m and by conducting polymer is meant a polymer with a conductivity of at least 10 S/m Hereby is obtained a biosensor, which can be used for routine medical check-up, thereby greatly reducing the cost and time per analysis, allowing more people to be screened for different diseases both inside and outside of medical facilities. Thus, by the biosensor is provided an effective point-of-care biosensor to detect, control and confine the spread of virulent diseases in the near future.

Further, the biosensor provides a fast, sensitive, reliable and selective method for analysis of non-human sample types, such as e.g. water samples possibly containing bacteria.

The target substance, which is detectable with the biosensor according to the above-mentioned method, may be a target molecule, nanoparticles, viruses, bacteria, chemicals, antibiotics, fertiliser or medicines in general and is thus not limited to being a biological sample. A large variety of target substances may be selectively detected upon choosing the correct corresponding probes.

The selective binding of the target substance facilitated by the probe ensures that only the target of interest is detected in the sample. This is a clear advantage compared to using a non-specific biosensor, where e.g. a known cell is attached directly to a non-specifically binding surface, and the subsequent influence of the virus infection on the cell is studied as disclosed in 'Polymer based biosensor for rapid electrochemical detection of virus infection of human cells' by Kiilerich-Pedersen et al published in Biosensors and Bioelectronics, vol. 28 (2011), p. 386-392.

By covalently coupling the probe to the electrode surface it is ensured that it does not detach. Electrochemical impedance spectroscopy also requires the binding event to be in close proximity to the surface. A direct link to the conductive polymer thus provides a defined distance of the binding event to the electric transducer.

As impedance spectroscopy is used for the direct detection of target substances binding to the electrodes, thus there is no need for adding any tag or redox mediator for the selective sensing for the detection to work.

The biosensor is an all-in-one device, where the sample is added to the biosensor instead of the biosensor having to be placed in a sample solution. Further as the biosensor includes both a primary electrode acting as the working electrode and a secondary electrode acting as a counter electrode, the need for additional electrodes—as used in conventional three electrode electrochemical cells—is absent. This reduces the amount of material needed for the device at the same time making the device highly adequate for mass production. Thus, production cost is reduced.

The electrodes in the biosensor are not metal based, which provides for a low material cost. The biosensor may consequently be used as a disposable device, which is advantageous when using the biosensor for point-of-care testing in a location, e.g. an airport, a school or a workplace, where multiple people need to be tested for a given virus and adequate cleaning of the biosensor between testing different people is impossible. Since it is a non-metal device, the used biosensor can be burned along with other types of biochemical waste, as there is no need for metal recovery.

Further, the biosensor only needs to be filled with the sample solution and connected electrically to a docking station. The detection results obtained by using the biosensor can thus be obtained in significantly shorter time with much less subsequent lab work as compared to standard testing methods such as e.g. ELISA and PCR. This makes the biosensor highly applicable in point-of-care methods and on-site measurements.

Thus, the biosensor according to the invention makes the process of detecting a specific target substance/object effortless due to the fact that the measurements now can take place on a localized electrode surface in contrast to targeting the point of interest in a solution e.g. using a standard three electrode electrochemical cell. This is especially advantageous when detecting target substances in small amounts of samples.

In one or more embodiments the primary electrode comprises a plurality of primary legs and the secondary electrode comprises a plurality of secondary legs, the primary legs and the secondary legs forms an interwoven pattern. The two electrodes are thereby in the same plane making calibration of the two in relation to each other unnecessary.

In one or more embodiments the second non-conducting substrate is provided with ports for inlet/outlet of the sample and/or for facilitating an electrical connection. The sample can thereby be added to the biosensor in a very easy manner, and likewise electrical connection to the electrodes in the biosensor is easily obtained by the ports.

In one or more embodiments the first substrate and/or the second substrate is a non-conducting polymer substrate. Alternatively, the first substrate and/or the second substrate can be a glass substrate or similar. The first and the second substrate can be in the same material, which can be beneficial production wise, but it is not a requirement.

In one or more embodiments the non-conducting polymer substrate is selected from the group of polystyrenes, polyolefins and cyclic olefin copolymers such as e.g. TOPAS 5013L (TOPAS Advanced Polymers, Germany).

In one or more embodiments the one or more conducting polymer layers of the conducting polymer electrode layer is selected from the group of poly(3,4-ethylenedioxythiophene) (PEDOT), polypyrrole (PPy), poly(3,4-propylenedioxythiophene), triacetonamine (TAA), polyaniline (PANI), derivatives thereof and/or co-polymers thereof.

In one or more embodiments the one or more conducting polymer layers of the conducting polymer electrode layer is selected from the group of PEDOT and PEDOT derivatives, which have shown to be highly stable with a high conductivity.

In one or more embodiments the PEDOT derivatives contain one or more functional groups selected from the group of alcohols (OH), carboxylic acids (COON), azides ($N_3$) and alkynes. These functional groups facilitate binding with the probe layer.

In one or more embodiments the conducting polymer electrode layer comprises a first conductive polymer layer and a second conducting polymer layer, wherein the probe layer is bonded to the second conducting polymer layer. The first conductive polymer layer may be PEDOT and the second conducting polymer layer may be a PEDOT-derivative for facilitating improved binding with the probe layer.

In one or more embodiments the probe layer is covalently bonded to part of the primary electrode surface, thereby creating a strong bond between the probe layer and the electrode layer.

In one or more embodiments the probe layer comprises an entity selected from the group of aptamers, oligonucleotides and/or peptides. Probes of aptamers, oligonucleotides and/or peptides are a superior substitute to probes comprising antibodies in immunoassays, since aptamers, oligonucleotides and peptides have a higher stability, affinity, and specificity compared to antibodies in immunoassay. As aptamers, oligonucleotides and peptides are significantly smaller in size than their antibody counter parts, the target substances captured by an aptamer, oligonucleotide and/or peptide probe will be much closer to the polymer layer than if using antibodies as probes. As a consequence, the change in the impedance signal due to the capture of the target substance by an aptamer, oligonucleotide and/or peptide probe will be much stronger, enabling a more precise detection result, and higher sensitivity.

In one or more embodiments the electrode layer comprises a second electrode pair comprising a second primary electrode and a second secondary electrode. The probe layer is normally not bonded to the secondary electrode pair, thereby serving as a reference electrode.

Disclosed herein is further the use of a biosensor for point-of-care measurement and/or on-site detecting of a target substance in a liquid sample such as e.g. water, blood, urine and saliva.

Also disclosed herein is a system for detection of a target substance in a sample, the system comprising a biosensor, a docking station, and connectors for operational connection between the docking station and the biosensor, wherein the docking station measures changes in the impedance over the first and/or second electrode pair before and after applying sample to the biosensor. By docking station is meant an apparatus for measuring the current over and/or imposing a current through the system, e.g. an apparatus which imposes a small sinusoidal voltage at a certain frequency to the biosensor and measures the resulting current through the biosensor. Hereby is obtained a fast, sensitive, reliable and selective impedance biosensor-based system for fast, cheap, and reliable point-of-care diagnostics and on-site measurements.

DETAILED DESCRIPTION

Figure 1A:
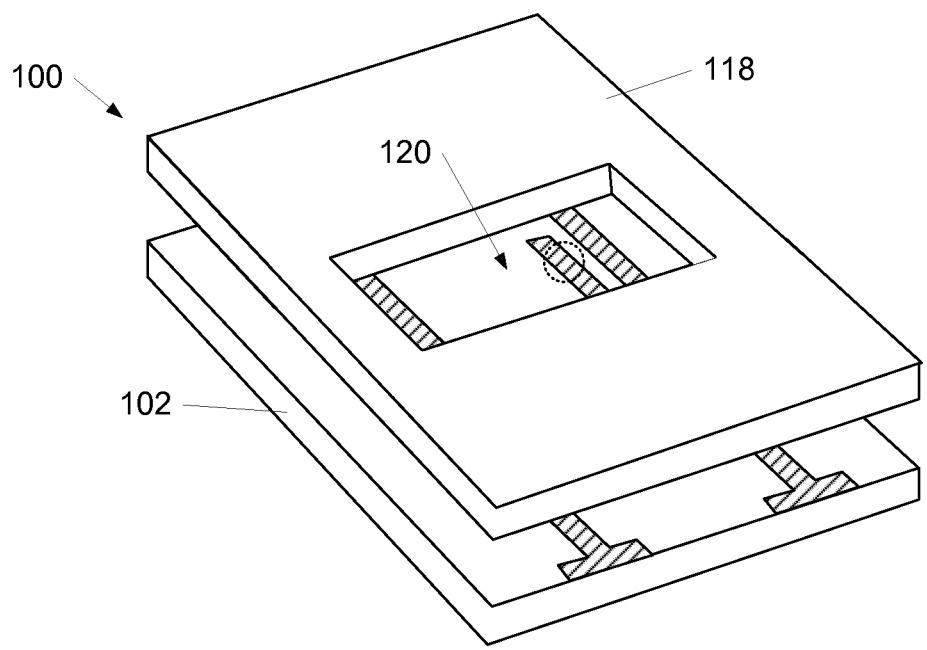
FIGS. 1a-b are schematic illustrations of a biosensor with a non-limiting electrode design according to the invention displayed in a perspective view with (1a) and without (1b) the second substrate layer.
Figure 1B:
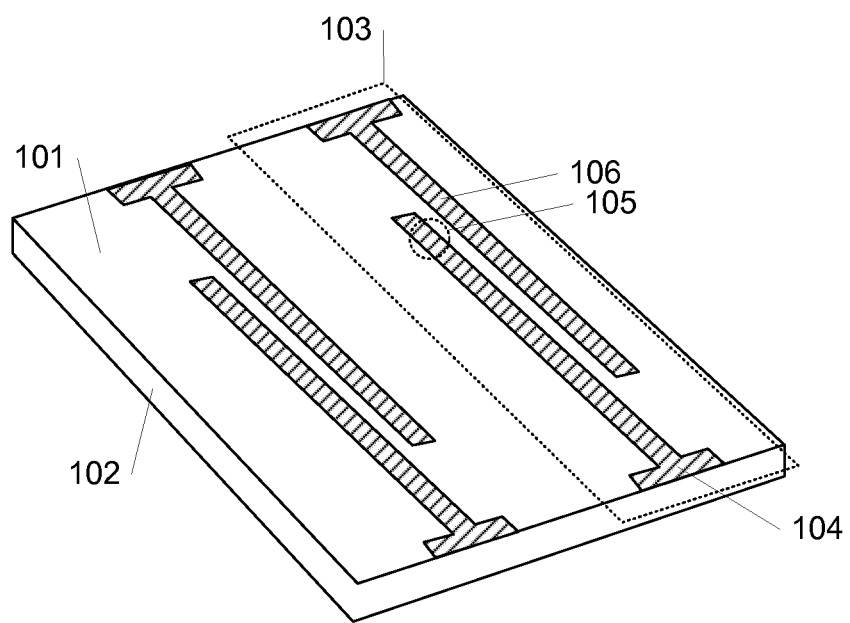

FIG. 1a-b illustrate the basic layout of a biosensor 100 according to the invention as seen in a perspective view with (FIG. 1a) and without (FIG. 1b) the second substrate layer.

The biosensor 100 for detection of a target substance in a sample comprises a first non-conducting substrate 102 comprising a primary substrate surface 101. The biosensor 100 further comprises a conducting polymer electrode layer 108 comprising one or more conducting polymer layers, the conducting polymer electrode layer comprising a primary electrode surface and a secondary electrode surface, wherein the secondary electrode surface covers part of the primary substrate surface 101.

The biosensor further comprises a probe layer 110 bonded to part of the primary electrode surface and a second non-conducting substrate 118 comprising a secondary substrate surface, wherein the secondary substrate surface of the second substrate and the primary substrate surface of the first substrate are interconnected such that the electrode layer and the probe layer are confined within an area defined by the first substrate and the second substrate.

The electrode layer 108 comprises at least a first electrode pair 103, the first electrode pair comprising a primary electrode 104 and a secondary electrode 106, where the probe layer 110 is bonded to the primary electrode 104 and/or the secondary electrode 106 of the at least first electrode pair 103.

On top of the first substrate layer 102 and the electrodes 104, 106 is a second substrate layer 118. The two substrate layers 102, 118 are of a non-conducting material such as a non-conducting polymer, glass or similar. Some examples of non-conducting polymers are polystyrenes, polyolefins and cyclic olefin copolymers such as e.g. TOPAS 5013L (TOPAS Advanced Polymers, Germany).

The second substrate layer 118 has an opening 120 forming a channel allowing samples to come in contact with the electrodes 104, 106. The electrodes 104, 106 are made from conducting polymers and are thus not metal based. Non-limiting examples of suitable conducting polymers with high conductivity and high stability are polypyrrole (PPy), poly(3,4-ethylenedioxythiophene) (PEDOT), poly(3, 4-propylenedioxythiophene), triacetonamine (TAA), polyaniline (PANI), derivatives thereof and/or co-polymers formed by two or more of the monomeric units in the mentioned polymer examples.

Non-limiting examples of functional groups in the derivatives, e.g. the PEDOT derivatives, are alcohols (OH), carboxylic acids (COOH), azides ($N_3$) and alkynes.

Figure 3:
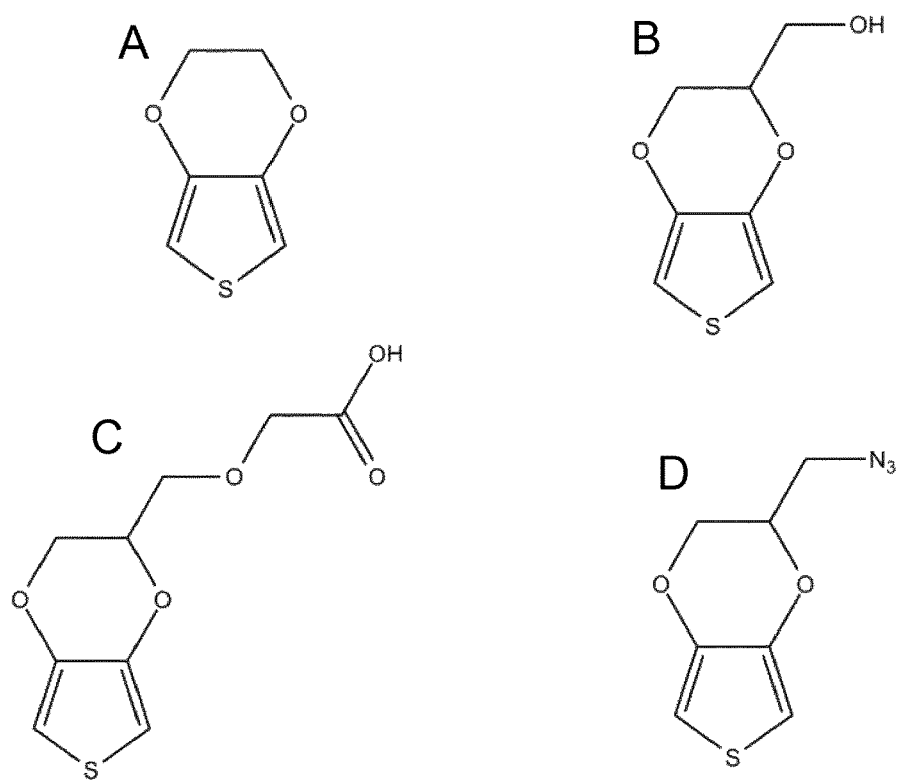
FIG. 3 shows the structure of four different monomer building blocks; A) EDOT, B) EDOT-OH, C) EDOT-COON, and D) EDOT-$N_3$.

FIG. 3 shows 3,4-ethylenedioxythiophene (EDOT) (FIG. 3A) and the OH, COOH, and $N_3$ based EDOT-derivatives; EDOT-OH (FIG. 3B) EDOT-COOH (FIG. 3C) and EDOT-$N_3$ (FIG. 3D) used as the monomeric building block for PEDOT, PEDOT-OH, PEDOT-COOH, and PEDOT-$N_3$, respectively.

Figure 4:
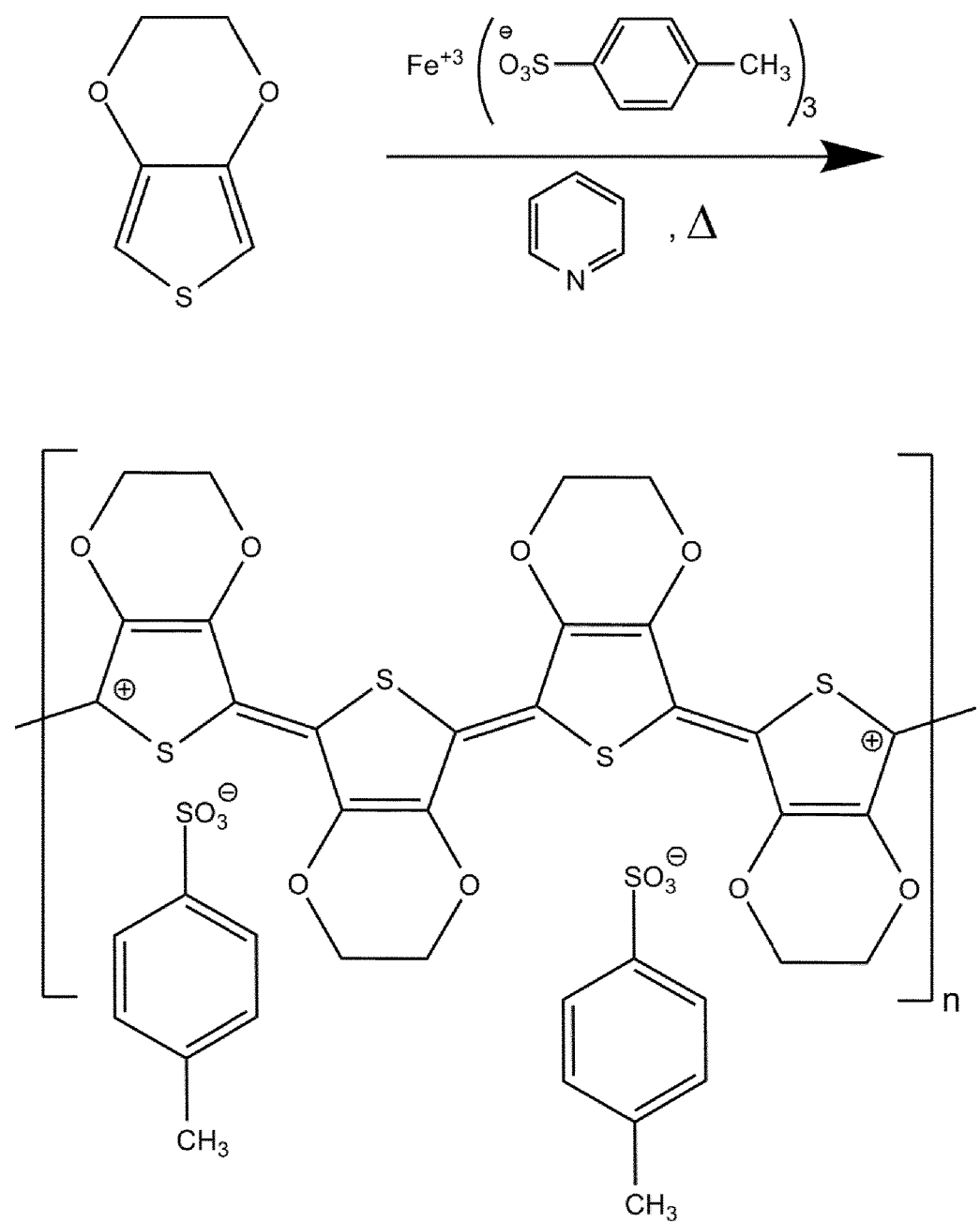
FIG. 4 illustrates the synthesis of PEDOT.

The synthesis of PEDOT (and similarly for derivatives thereof) can be done using different polymerization schemes starting from EDOT monomer. FIG. 4 shows one possible synthesis way, wherein Fe(III) p-toluene sulfonate (iron tosylate) is used for the oxidative chemical polymerization of the EDOT monomer. To inhibit the spontaneous oxidation of the monomer by iron tosylate, pyridine can be added to the solution. The substrate can then be spin coated on the support wafers. By heating, the inhibitor evaporates and the oxidative polymerisation of EDOT starts, whereby PEDOT is formed. Fe(II)-salts formed under polymerization are washed away afterwards by rinsing with water, leaving the doped conducting form of PEDOT, which is insoluble in any common solvent, transparent and mechanically durable.

Figure 2:
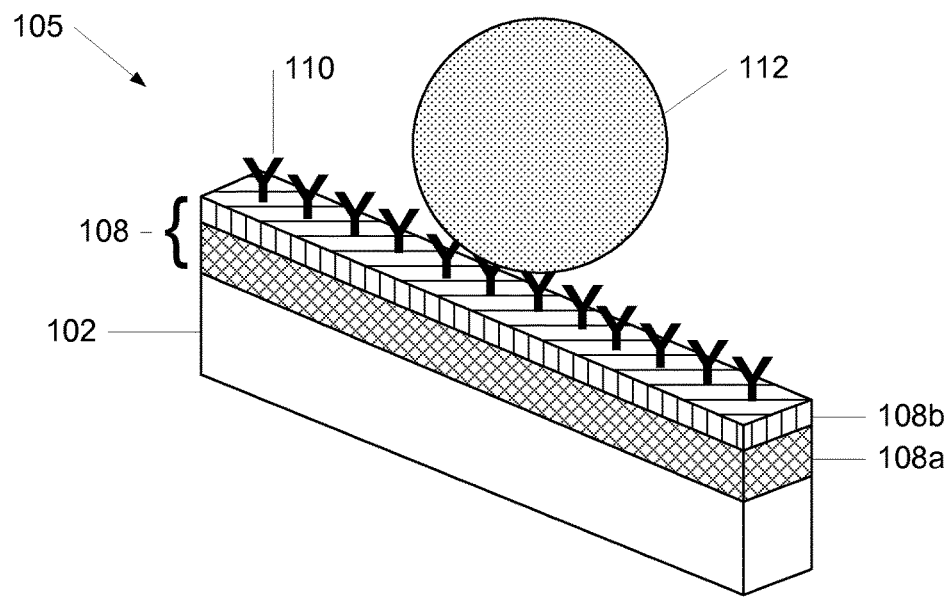
FIG. 2 shows an enlargement of the electrode of the biosensor in FIGS. 1a-b displayed in a perspective view.

The electrodes 104, 106 shown in FIG. 1 may comprise one layer of a conducting polymer or multiple layers of the same or different conducting polymers. FIG. 2 shows an enlargement view 105 of part of the primary electrode 104 functioning as the working electrode, wherein the polymer layer 108 coated onto the first substrate layer 102 comprises two layers of polymers; a first polymer layer 108a of e.g. PEDOT and a second polymer layer 108b of e.g. the PEDOT-derivative hydroxymethyl-PEDOT (PEDOT-OH). The secondary electrode 106 is constructed in a similar manner and functions as a counter electrode.

Covalently bound to the polymer layer 108 is a probe layer 110 comprising an entity such as an aptamer, an oligonucleotide and/or a peptide. The entity in the probe layer 110 binds selectively to a specific target substance 112. The target substance could be a virus, a protein, a cell, a peptide, a molecule (both organic and inorganic), a structured nano-particle, an antibiotic, a fertiliser or similar. Thereby, when a sample, such as e.g. a blood sample, urine and saliva, or water, containing target substances 112 come in contact with the biosensor 100 (by adding the sample to the opening(s) 120 in the biosensor), the target substances 112 will form bonds, e.g. ionic bonds, hydrogen bonds or other electrostatic interaction bonds, with the probe 110.

For specific detection of target objects such as DNA strands and proteins, an aptamer, oligonucleotide and/or peptide probe 110 is a superior substitute compared to probes comprising antibodies, since aptamers, oligonucleotides and peptides have a higher stability, affinity, and specificity compared to antibodies. As aptamers, oligonucleotides and peptides are significantly smaller in size than their antibody counter parts, the target substances captured by an aptamer/oligonucleotide/peptide probe will be much closer to the polymer layer 108 than when using antibody in immunoassay as probe. As a consequence, the change in the impedance signal due to the capture of the target substance 112 by an aptamer/oligonucleotide/peptide probe will be much stronger, enabling a more precise detection result.

In contrast to enzymes or antibodies, aptamers e.g. have a capability to bind a wide range of targets: nucleic acids, proteins, ions, toxic substances, viruses, cells and other compounds with high affinity and sensitivity.

Aptamers are peptides or oligonucleotides (RNA or single stranded DNA) which typically fold into a three-dimensional structure, and whose conformation is changing upon ligand binding. Novel aptamers can be developed using a process called SELEX (Systematic Evolution of Ligands by Exponential enrichment). It enables the selection of high-affinity nucleic acid sequences from a random pool of candidates. The oligonucleotide aptamers can easily be modified with signal moieties and can be produced at low cost. Thus, the probe 110 may be a biological entity or a synthetically produced replica and/or modification of such.

The second polymer layer 108b, which binds covalently to the probe 110 is normally chosen such that it facilitates an improved binding capacity for forming covalent bonds between the second polymer layer 108b and the probe 110. Depending on production cost and productions lines, a single polymer layer of e.g. PEDOT-OH may be preferable over the double layering design shown in FIG. 2.

Figure 5:
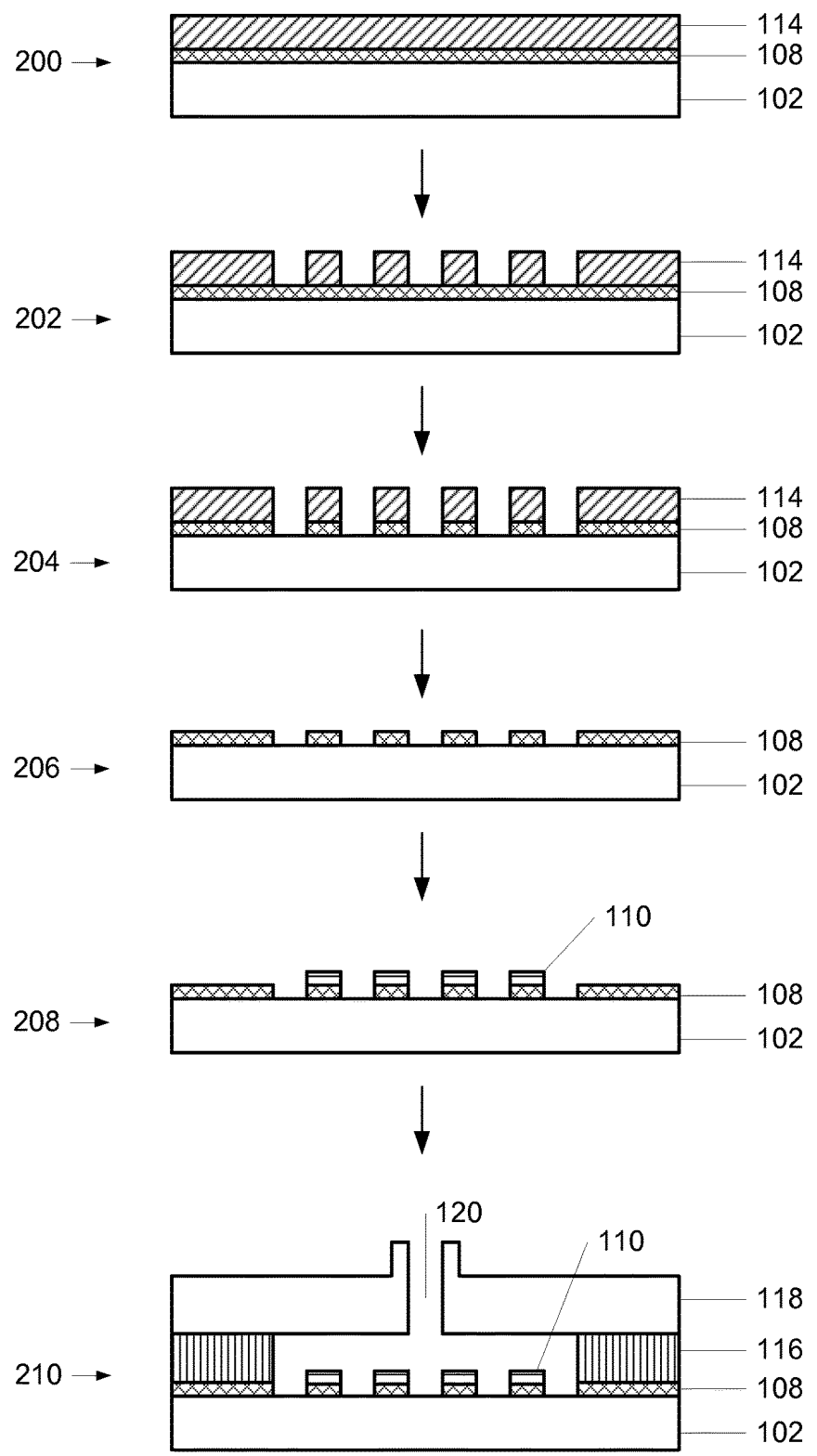
FIG. 5 shows the steps involved in producing a biosensor according to the invention using one possible production method. The biosensor is illustrated in a side view.

FIG. 5 illustrates the steps involved in one possible method for the production of the all polymer biosensor according to the invention. The first substrate layer 102 in the wafer 200 is a non-conductive substrate layer 102 fabricated from e.g. the cyclic olefin copolymer TOPAS 5013L (TOPAS Advanced Polymers, Germany) by injection moulding.

After rinsing the substrate layer 102 with isopropanol, ethanol and demineralised water, a polymer layer 108 of e.g. PEDOT and/or PEDOT derivatives is spun upon the substrate 102 at 1000 rpm for 20 seconds to achieve a height of approximately 100-400 nm. Higher or lower heights of the polymer layer 108 could also be obtained. The substrate 102 with the polymer layer 108 is subsequently placed in a nitrogen oven for approximately 2-10 minutes at 70° C. and next rinsed thoroughly with demineralised water.

PEDOT and derivatives thereof are examples of homopolymers, where the polymer comprises one type of monomer unit. As an alternative to homopolymers, the polymer layer 108 could also be a co-polymer comprising two or more different monomer units. Non-limiting examples of other suitable conducting polymers with high conductivity and high stability are polypyrrole (PPy), poly(3,4-propylenedioxythiophene), triacetonamine (TAA), polyaniline (PANI) derivatives thereof and/or co-polymers formed by two or more of the monomeric units in the mentioned polymers possibly in combination with PEDOT and/or PEDOT derivatives.

A positive photoresist 114, such as e.g. S1813 (Shipley Company, USA), is spun on the polymer layer 108 at 3000 rpm for 30 seconds, thereby creating a protective layer with the height of approximately 1500 nm. The photoresist 114 is formed in a predetermined pattern for creating a preselected primary/secondary electrode design in the electrode pair(s) 103 for obtaining a working/counter electrode pair. To harden the photoresist, the wafer 200 is placed in a nitrogen oven for 10 minutes at 70° C. This insures that excess solvent evaporates from the photoresist 114.

By exposing the wafer 200 to UV light for 35 seconds (at 275 W and 5:98 mJ/cm$^2$) the preselected pattern in the wafer is produced yielding the wafer 202. Reactive ion etching creates the preselected pattern in the polymer electrode layer 108 as shown in the wafer 204. The photoresist 114 is subsequently removed by flood exposing the wafer 204 with UV light and then removing the photoresist 114 with a four minute ethanol bath thereby obtaining the wafer 206.

Alternatively to the above, the electrode pattern can be formed by other standard methods of photolithography.

A probe is covalently bound to the polymer layer 108 normally by flushing a liquid containing the probe through the wafer thereby leaving the probes 110 on the polymer layer 108. The probe is selectively chosen for binding with the target substance, e.g. a virus, to be detected in a given sample. Examples of suitable probes include peptides, aptamers and/or oligonucleotides.

As an alternative to flushing the probe solution through the water, the polymer layer 108 can first be modified with succinic anhydride to have an acid group rather than a hydroxyl group, and then afterwards further activate the acid group using the standard EDC/NHS (1-ethyl-3-(3-dimethylaminopropyl)carbodiimide/N-hydroxysuccinimide) method. The further activated acid group can then react with the amino-terminated probe.

A second substrate layer 118 may be secured to the wafer 208 by use of e.g. a transfer adhesive 116 thereby yielding the biosensor 210. Alternatively, the transfer adhesive 116 layer can be abandoned if there are sample channels in the second substrate layer 118 allowing the second substrate layer 118 and the first substrate layer 102 to be connected directly.

The second substrate layer 118 contains access ports 120, e.g. in standard Luer lock size, for fluid inlets, outlets and/or electrical connections. The second substrate layer 118 is a non-conductive substrate layer (similarly to the first substrate layer 102) fabricated from e.g. the cyclic olefin copolymer TOPAS 5013L (TOPAS Advanced Polymers, Germany) by injection moulding.

The second substrate layer 118 and the first substrate layer 102 are preferably in the same material for reduced production costs. The second substrate layer 118 may also be patterned in a channel area situated opposite the patterned area 302 in the first substrate layer 102 when the two parts are assembled. This is beneficial production wise, as the second substrate layer 118 and the first substrate layer 102 can be produced in the same production line. Also, the patterned design forces the sample substances to distribute more evenly and thereby bind more efficiently to the probe 110 attached to the polymer 108.

Alternatives to the lithography biosensor production method producing the patterned electrode design as described in connection with FIG. 5 are methods such as stamping, ink-jet printing, screen printing or similar.

The probe 110 can be applied before or after assembling the second substrate layer 118 and the first substrate layer 102. This is highly advantageous in mass production, because the target substance specificity of the biosensor can be selected after the production process. This can provide for an extremely fast production of biosensors with probe selectivity for a specific virus for example in case of an epidemic situation.

Figure 6A:
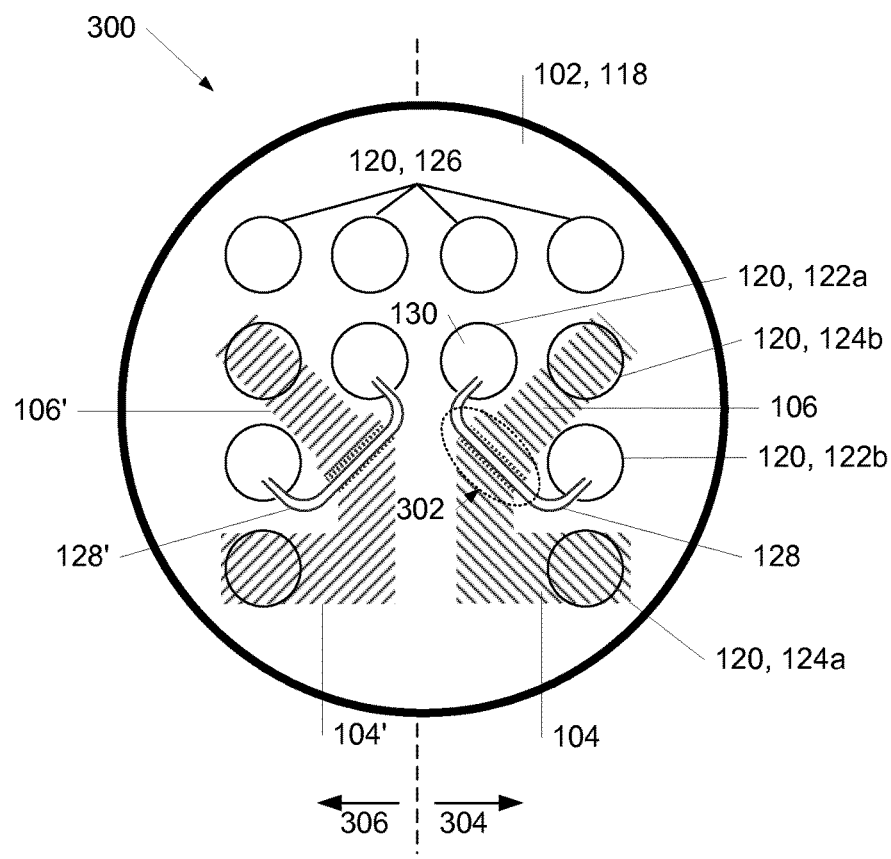
FIG. 6a shows an embodiment of the biosensor viewed from the top.
Figure 6B:
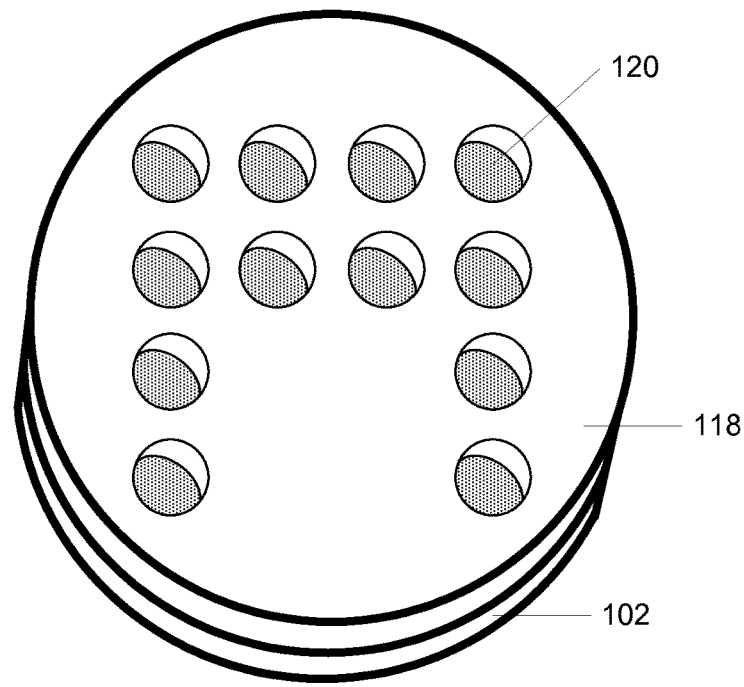
FIG. 6b shows the second substrate layer in a perspective view.

FIG. 6a shows an embodiment of the biosensor 300 according to the invention seen in a top down view where the second substrate is shown as a see-through object. FIG.

6b shows the second substrate 118 in a perspective view clearly showing the access ports 120 in the second substrate 118 for sample inlet/outlet and for providing electrical connections.

The biosensor 300 comprises a first substrate layer 102 and a second substrate layer 118, the latter comprising access ports 120 in standard Luer lock size. Two of the ports 122a, 122b provide inlet/outlet openings for the sample possibly containing target substances. Connection between the two inlet/outlet ports 122a, 122b is facilitated by a channel 128 formed in the second substrate layer 118 and/or the first substrate layer 102.

Electrical connection between the primary electrode 104 (acting as the working electrode) and the secondary electrode 106 (acting as the counter electrode) is provided through the electrode ports 124a and 124b, respectively, using connectors. The connectors further provide for operational connection between a docking station and the biosensor. By docking station is meant an apparatus for measuring the current over and/or imposing a current through the system, e.g. an apparatus which imposes a small sinusoidal voltage at a certain frequency to the biosensor and measures the resulting current through the biosensor.

A patterned electrode design, e.g. created by the method described in FIG. 5, is present in the sensing area 302 of the biosensor 300 where the primary electrode 104, the secondary electrode 106 and the sample channel 128 overlap, thereby creating an interwoven electrode pattern.

Figure 7A:
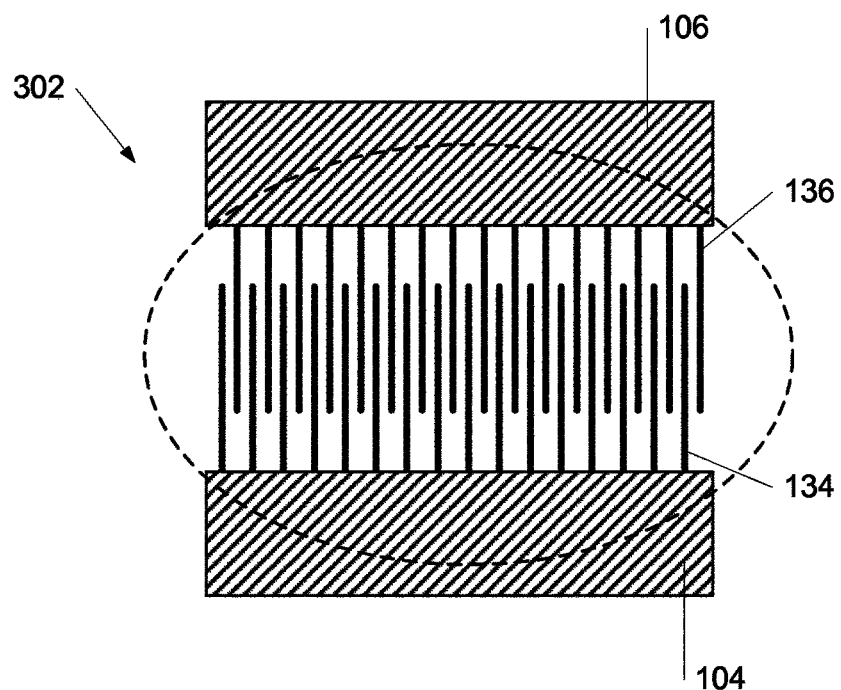
FIGS. 7a-b illustrate different working/counter electrode design options.
Figure 7B:
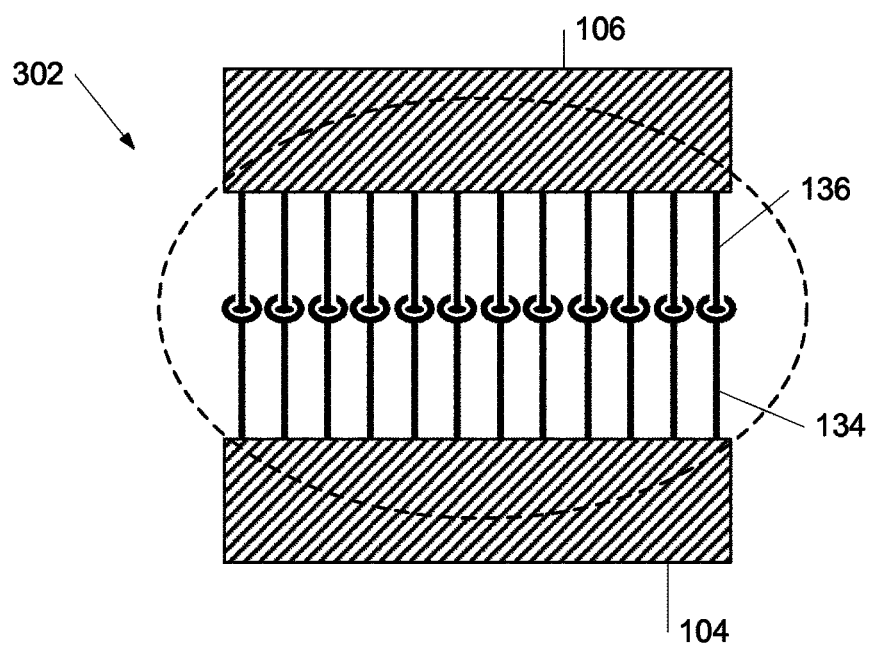

FIGS. 7a and 7b are enlargement top-down views of the interwoven electrode array design (found in the sensing area 302 marked in FIG. 6a) showing different examples of possible primary electrode 104 and secondary electrode 106 designs. In FIG. 7a the primary electrode legs 134 and the secondary electrode legs 136 form a woven leg pattern. In FIG. 7b a different design is shown and many other design options could also be possible.

The ports 126 seen as an upper line in FIG. 6a are in the shown embodiment not used for detection of target substances. Instead the ports 126 represent the option that multiple electrode pairs 103 and sample channels 128 can be present. This will allow for simultaneous detection of more than one target substance by using different probes 110 attached to the polymer layer 108 in different electrode pairs 103.

Detecting several targets with one device is favourable for reducing cost, time and number of samples necessary for the test. In order to ensure that only one type of probe is attached to one set of electrode pairs 103, different polymers selectively forming covalent bonds with specific probes could be used for the different electrode pairs 103. Alternatively, physically blocking access to all but one set of electrode pairs 103 could also ensure that the probe only binds to the polymer in this set of electrode pairs 103. The latter method is preferable if different probes are capable of forming covalent bonds with the same polymer.

Physically blocking access to all but one set of electrode pairs also allows for the use of the same polymer in all the electrodes pairs, thereby reducing production costs and complications regarding different conductivities. The multiple port design shown in FIGS. 6a and 4b makes it possible to covalently bind different probes to different electrode pairs by using different ports connected two and two each by an individual sample channel 128.

The biosensor 300 shown in FIG. 6a has two symmetric sides; the measurement side 304 and the reference measurement side 306. The only difference between the electrodes 104, 106 and the sample channel 128 on the measurement side 304 and the electrodes 104', 106' and channel 128' on the reference side 306 is that the measurement side electrodes 104, 106 has a probe 110 covalently bound to the polymer layer 108, whereas the reference side electrodes 104', 106' lack the probe.

When a sample containing a target substance is added to the channels 128, 128' on both the measurement side 304 and the reference side 306, the target substances 112 will bind to the probe 110 on the electrodes 104, 106 on the measurement side 304, but not to the electrodes 104', 106' on the reference side 306. This will introduce a change in the impedance on the measurement side 304 but not on the reference side 306. The difference in the impedance measured on the measurement side 304 and the reference side 306 thereby provides a direct indication of the amount of target substance in the sample. Thus, the presence of a target substance 112 in a sample can be detected very efficiently with a biosensor according to the invention by using EIS.

Contributions to the impedance from target substances 112 binding directly to the polymer layer 108 are also eliminated by measuring the impedance both on the reference side 306 and the measurement side 304 of the biosensor 300.

The impedance biosensor incorporates both the primary electrode 104 and the secondary electrode 106 and does not necessitate an extra reference electrode. This makes the process of detecting a specific substance extremely simple due to the fact that the measurements can take place using only one electrode pair instead of the standard three-electrode electrochemical cell. This is especially advantageous when detecting target substances in small amounts of samples, as using a standard three-electrode electrochemical cell requires a relatively large sample volume in order to a reliable result.

The all-polymer biosensor is further easily mass-produced and holds several other advantages such as high integration, low sample- and reagent volume, short analysis time, low sample waste and low material cost.

Low material cost, obtained among others by using non-metal based electrodes, further allows the biosensor to be used as a disposable device. This is advantageous, if the biosensor is used for point-of-care testing in a location, e.g. an airport, a school or a workplace, where multiple people need to be tested for a given virus and adequate cleaning of the biosensor in between testing different people is impossible.

Alternatively, the probe can be heated or treated with a high concentrated salt solution in order to release the target substance, whereby the biosensor can be used multiple times.

The biosensor shown in FIG. 6a is typically 3-10 cm in diameter and 0.5-2 cm thick. The sample volume required for obtaining a reliable result is approximately 10-200 µl.

The detection of target substances in a sample using the biosensor and EIS is an advantageous method as it eliminates the need for labelling the target substance due to the fact that the binding event is detected directly by a change in the surface properties of the electrode. Thus, impedance biosensors are favourable due to their high sensitivity and ability to perform label free detection. Labelling a biosubstance can drastically change its binding properties, thereby giving a highly variable detection results.

Figure 8:
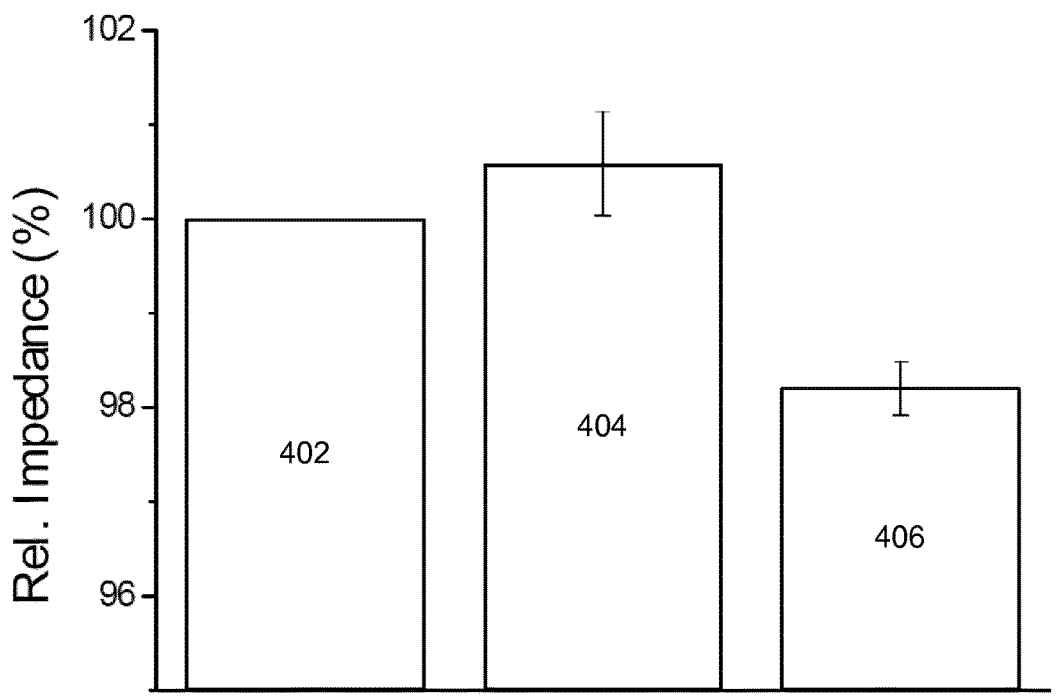
Figure 9:
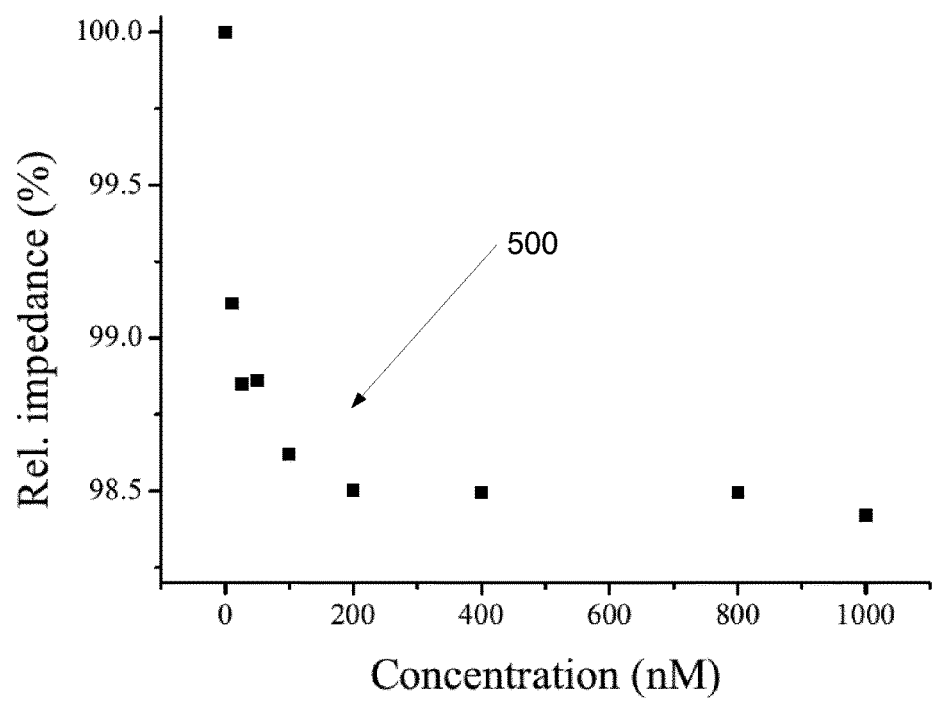
Figure 10:
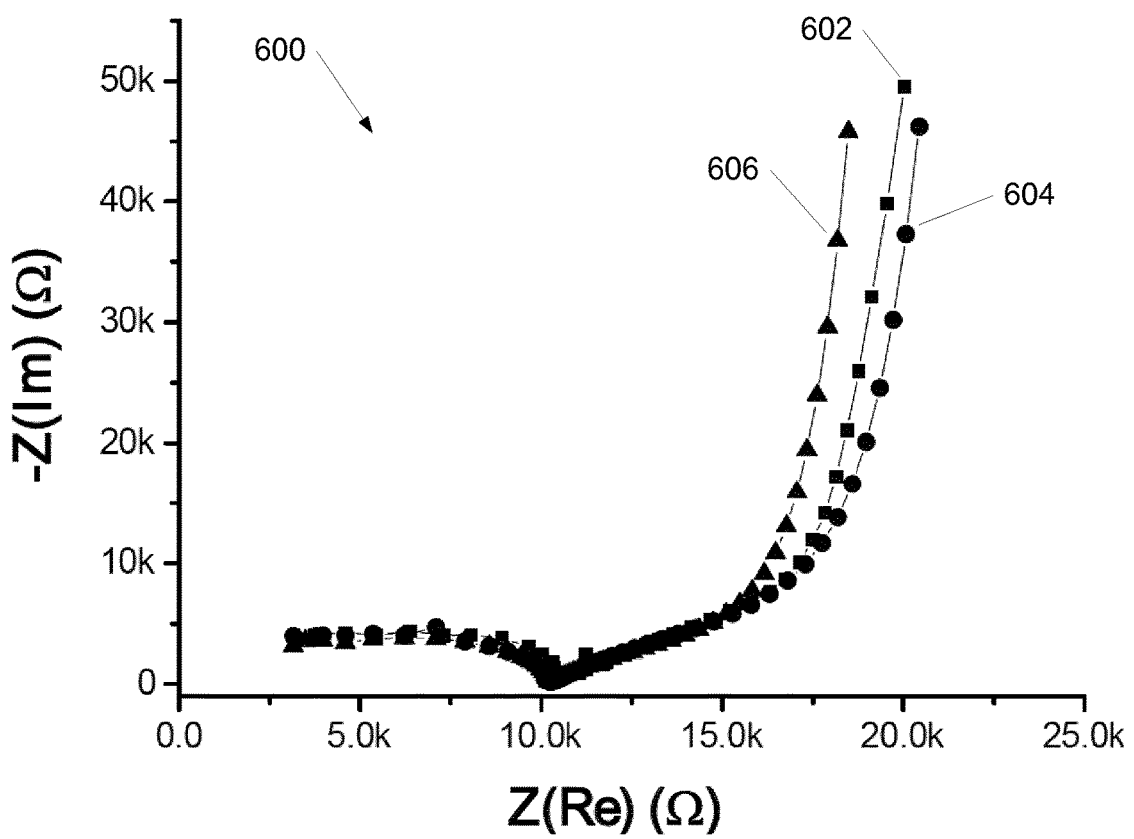

FIGS. 8-10 show measurements conducted on an all-polymer biosensor using Topas as the non-conducting polymer substrate and tosylate doped poly(3,4-ethylenedioxythiophene) (PEDOT:TsO) as the electrode material. The electrode material is covalently functionalized with two different aptamers as probes for studying the selective capture of correspondingly two different target substances; the antibiotics ampicillin and kanamycin.

The measurements of the impedance changes were performed by connecting an impedance spectrometer (VersaSTAT 3, Princeton Applied Research, USA) to the electrodes by spring-loaded (Pogo Pin) contacts. The impedance of the system was measured with two methods: single frequency time scans at 501 mHz as shown in FIG. 8 and wide spectrum sweeps with a frequency range from 1 MHz to 251 mHz (logarithmic scale with 10 points per decade) as shown in FIG. 10. After the baseline was recorded the target was added and the change of the impedance signal monitored.

FIG. 8 shows the impedance changes measured at 501 mHz of the biosensor without having an antibiotic immobilized on patterned surfaces 402, after binding of 1 μM kanamycin 404 to its corresponding aptamer, and after binding of 1 μM ampicillin 406 to its corresponding aptamer.

Measuring the impedance as shown in FIG. 8 can not only give us information about the fact that a binding event has taken place, but it can also give us an insight in the change caused by the binding event. The immobilization of the aptamers alone provoked an increase in the impedance, as expected. Furthermore, we observed two distinct and reproducible responses from our sensor with the two different aptamer-target binding events: The kanamycin binding to the corresponding aptamer caused an increase in the impedance measured at a single frequency (501 mHz) relative to the pristine state (only the aptamer is immobilized on the surface), while adding ampicillin to a sensor equipped with the corresponding aptamer lead to a decrease of impedance.

Control experiments, where the antibiotics were reacted with the mismatching aptamers, gave no changes in the impedance signal. After that, injecting the matching antibiotics into the biosensor resulted in the expected increase or decrease of impedance. This fact shows that the immobilization of the aptamers on the electrodes didn't affect the ability of specific binding to their target.

The total impedance change at 1 μM concentration was in average +0.6% for kanamycin 404 and −2.4% for ampicillin 406. The sensitivity is strongly dependent on the effective wire size.

FIG. 9 shows the measurement 500 made in an analyte concentration range between 10 nM-1 μM of ampicillin. For ampicillin in concentrations above 200 nM no further decrease of impedance is detectable, which means that the sensor is saturated at that point. For kanamycin, the lower detection limit is around 500 pM target concentration (not shown in the figure).

The curve 500 shows that there is a logarithmic relation between the analyte concentration and the change of impedance. Because of the strong binding of the target to the aptamers the sensor is not suited for continuous detection in a passing fluid. The analyte would accumulate and saturate the available probes after a certain time.

The range represented in FIG. 9 reaches from 10 nM to 1 μM, but detection of ampicillin in a concentration as low as 500 pM is also possible. Thus, the biosensor presented here also has the capability of quantitative analyte detection.

The wide spectrum swept with a frequency range from 1 MHz to 251 mHz (logarithmic scale with 10 points per decade) is shown as a Nyquist plot in FIG. 10 for the biosensor with the aptamer and no target molecule bound thereto 602, the biosensor with kanamycin bound to its specific aptamer 604, the biosensor with ampicillin bound to its corresponding aptamer 606.

LIST OF REFERENCES 100 biosensor
101 primary surface of the first substrate layer
102 first substrate layer
103 electrode pair
104, 104' primary electrode, acting as working electrode
105 part of the primary electrode
106, 106' secondary electrode, acting as counter electrode
108 polymer layer
108a first polymer layer
108b second polymer layer
110 probe
112 target substance
114 photoresist
116 adhesive
118 second substrate layer
120 opening, port
122a, 122b port for the sample
124a, 124b port for providing electrical connection
126 port not in use
128, 128' channel connecting sample ports
130 sample
134 primary electrode legs
136 secondary electrode legs
300 biosensor
302 sensing area of the biosensor
304 measurement side of the biosensor 300
306 reference side of the biosensor 300
402 impedance changes without an immobilized target
404 impedance changes after binding of 1 μM kanamycin
406 impedance changes after binding of 1 μM ampicillin
500 concentration dependency in the impedance changes
600 Nyquist plot
602 the aptamer and no target molecule
604 kanamycin bound to its specific aptamer
606 ampicillin bound to its corresponding aptamer

The invention claimed is:

1. A biosensor for detection of a target substance in a sample with impedance spectroscopy, the biosensor comprising:
   a first non-conducting substrate comprising a primary substrate surface;
   a conducting polymer electrode layer comprising one or more conducting polymers layers, the conducting polymer electrode layer comprising a primary electrode surface and a secondary electrode surface, wherein the secondary electrode surface covers part of the primary substrate surface;
   a probe layer bonded to part of the primary electrode surface; and
   a second non-conducting substrate comprising a secondary substrate surface, wherein the secondary substrate surface of the second substrate and the primary substrate surface of the first substrate are interconnected such that the electrode layer and the probe layer are confined within an area defined by the first substrate and the second substrate;
   wherein the electrode layer comprises at least a first electrode pair, the first electrode pair comprising a primary electrode and a secondary electrode, the primary electrode and the secondary electrode being non-overlapping, and wherein the probe layer is bonded to the primary electrode and/or the secondary electrode of the at least first electrode pair, the probe layer being adapted for selectively binding of the target substance.

2. A biosensor according to claim 1, wherein the primary electrode comprises a plurality of primary legs and the secondary electrode comprises a plurality of secondary legs, the primary legs and the secondary legs forms an interwoven pattern.

3. A biosensor according to claim 1, wherein the second non-conducting substrate is provided with ports for inlet/outlet of the sample and/or for facilitating an electrical connection.

4. A biosensor according to claim 1, wherein the first substrate and/or the second substrate is a non-conducting polymer substrate.

5. A biosensor according to claim 4, wherein the non-conducting polymer substrate is selected from the group of polystyrenes, polyolefins and cyclic olefin copolymers such as e.g. TOPAS 5013L (TOPAS Advanced Polymers, Germany).

6. A biosensor according to claim 1, wherein the one or more conducting polymer layers of the conducting polymer electrode layer is selected from the group of poly(3,4-ethylenedioxythiophene) (PEDOT), polypyrrole (PPy), poly(3,4-propylenedioxythiophene), triacetonamine (TAA), polyaniline (PANI), derivatives thereof and/or co-polymers thereof.

7. A biosensor according to claim 1, wherein the one or more conducting polymer layers of the conducting polymer electrode layer is selected from the group of PEDOT and PEDOT derivatives.

8. A biosensor according to claim 7, wherein the PEDOT derivatives contain one or more functional groups selected from the group of alcohols (OH), carboxylic acids (COOH), azides ($N_3$) and alkynes.

9. A biosensor according to claim 1, wherein the conducting polymer electrode layer comprises a first conductive polymer layer and a second conducting polymer layer, wherein the probe layer is bonded to the second conducting polymer layer.

10. A biosensor according to claim 1, wherein the first conductive polymer layer is PEDOT and the second conducting polymer layer is a PEDOT-derivative.

11. A biosensor according to claim 1, wherein the probe layer is covalently bonded to part of the primary electrode surface.

12. A biosensor according to claim 1, wherein the probe layer comprises an entity selected from the group of aptamers, oligonucleotides and/or peptides.

13. A biosensor according to claim 1, wherein the electrode layer comprises a second electrode pair comprising a second primary electrode and a second secondary electrode.

14. A system for detection of a target substance in a sample, the system comprising a biosensor according to claim 1, a docking station, and connectors for operational connection between the docking station and the biosensor, wherein the docking station measures changes in the impedance over the first and/or second electrode pair before and after applying sample to the biosensor.

15. A biosensor according to claim 2, wherein the first substrate and/or the second substrate is a non-conducting polymer substrate.

16. A biosensor according to claim 2, wherein the one or more conducting polymer layers of the conducting polymer electrode layer is selected from the group of poly(3,4-ethylenedioxythiophene) (PEDOT), polypyrrole (PPy), poly(3,4-propylenedioxythiophene), triacetonamine (TAA), polyaniline (PANI), derivatives thereof and/or co-polymers thereof.

17. A biosensor according to claim 2, wherein the one or more conducting polymer layers of the conducting polymer electrode layer is selected from the group of PEDOT and PEDOT derivatives.

18. A biosensor according to claim 2, wherein the conducting polymer electrode layer comprises a first conductive polymer layer and a second conducting polymer layer, wherein the probe layer is bonded to the second conducting polymer layer.

19. A biosensor according to claim 2, wherein the first conductive polymer layer is PEDOT and the second conducting polymer layer is a PEDOT-derivative.

* * * * *